US007838029B1

(12) United States Patent  (10) Patent No.: US 7,838,029 B1
Ahmed et al.  (45) Date of Patent: Nov. 23, 2010

(54) MIRTAZAPINE SOLID DOSAGE FORMS

(75) Inventors: Salah U. Ahmed, New City, NY (US); Gandha V. Naringrekar, Princeton, NJ (US); Tahseen A. Chowdhury, Washington Township, NJ (US); Sudhir R. Gorukanti, Harriman, NY (US)

(73) Assignee: Watson Laboratories, Inc., Corona, CA (US)

( * ) Notice: Subject to any disclaimer, the term of this patent is extended or adjusted under 35 U.S.C. 154(b) by 0 days.

(21) Appl. No.: 10/902,836

(22) Filed: Aug. 2, 2004

Related U.S. Application Data

(60) Provisional application No. 60/491,279, filed on Jul. 31, 2003.

(51) Int. Cl.
*A61K 9/20* (2006.01)
*C07D 223/00* (2006.01)
(52) U.S. Cl. ...................... 424/464; 540/484
(58) Field of Classification Search ......... 424/464–465, 424/474–483, 489–502; 540/484
See application file for complete search history.

(56) References Cited

U.S. PATENT DOCUMENTS

| | | | |
|---|---|---|---|
| 4,062,848 A | 12/1977 | van der Burg |
| 5,082,864 A | 1/1992 | Van den Oetelaar et al. |
| 5,112,616 A | 5/1992 | McCarty |
| 5,178,878 A | 1/1993 | Wehling et al. |
| 5,208,261 A | 5/1993 | Van Den Oetelaar et al. |
| 5,238,688 A | 8/1993 | Beuving et al. |
| 5,464,632 A | 11/1995 | Cousin et al. |
| 5,725,884 A | 3/1998 | Sherwood et al. |
| 5,837,292 A | 11/1998 | Dijkgraaf et al. |
| 5,955,107 A | 9/1999 | Augello et al. |
| 5,958,453 A | 9/1999 | Ohno et al. |
| 5,977,099 A | 11/1999 | Nickolson |
| 6,024,981 A | 2/2000 | Khankari et al. |
| 6,040,301 A | 3/2000 | Skrabanja et al. |
| 6,114,324 A | 9/2000 | Skrabanja et al. |
| 6,150,353 A | 11/2000 | Broekkamp et al. |
| 6,211,171 B1 | 4/2001 | Sawynok et al. |
| 6,228,875 B1 | 5/2001 | Tsai et al. |
| 6,281,207 B1 | 8/2001 | Richter et al. |
| 6,294,198 B1 | 9/2001 | Vilkov |
| 6,303,595 B1 | 10/2001 | Andrews |
| 6,328,994 B1 | 12/2001 | Shimizu et al. |
| 6,376,668 B1 | 4/2002 | Iishi et al. |
| 6,399,310 B1 | 6/2002 | Murphy, Jr. et al. |
| 6,437,120 B1 | 8/2002 | Iishi et al. |
| 6,448,293 B1 | 9/2002 | Andrews et al. |
| 6,482,440 B2 | 11/2002 | Zemlan et al. |
| 6,495,685 B1 | 12/2002 | Maeda et al. |
| 6,545,149 B2 | 4/2003 | Singer et al. |
| 6,552,014 B2 | 4/2003 | Serebruany et al. |
| 6,552,189 B2 | 4/2003 | Iishi et al. |
| 6,576,764 B2 | 6/2003 | Singer et al. |
| 6,589,556 B2 | 7/2003 | Cherukuri |
| 6,610,747 B2 | 8/2003 | Adam et al. |
| 6,630,504 B2 | 10/2003 | Andrews et al. |
| 6,649,605 B2 | 11/2003 | Olesen et al. |
| 6,660,730 B2 | 12/2003 | Maeda et al. |
| 6,723,348 B2 | 4/2004 | Faham et al. |
| 6,723,845 B2 | 4/2004 | Iishi et al. |
| 6,774,230 B2 | 8/2004 | Metzger et al. |
| 2001/0009678 A1 | 7/2001 | Toshihiro et al. |
| 2001/0010825 A1 | 8/2001 | Shimizu et al. |
| 2002/0049233 A1 | 4/2002 | Kararli et al. |
| 2002/0052395 A1 | 5/2002 | Andrews et al. |
| 2002/0071864 A1 | 6/2002 | Kim et al. |
| 2002/0091129 A1 | 7/2002 | Boolell |
| 2002/0142034 A1 | 10/2002 | Shimizu et al. |
| 2002/0183303 A1 | 12/2002 | Andrews et al. |
| 2003/0017202 A1 | 1/2003 | Bunick et al. |
| 2003/0026835 A1 | 2/2003 | Nishii et al. |
| 2003/0035833 A1 | 2/2003 | He |
| 2003/0054037 A1 | 3/2003 | Babcock et al. |
| 2003/0054038 A1 | 3/2003 | Crew et al. |
| 2003/0060456 A1 | 3/2003 | Adam et al. |
| 2003/0072801 A1 | 4/2003 | Curatolo et al. |
| 2003/0099700 A1 | 5/2003 | Faham et al. |
| 2003/0104063 A1 | 6/2003 | Babcock et al. |

(Continued)

FOREIGN PATENT DOCUMENTS

EP  0 839 526 A2  5/1998

(Continued)

OTHER PUBLICATIONS

Marc Gordon, "Process Considerations in Reducing Tablet Friability and Their Effect on in vitro Dissolution", Jan. 1994, Drug Development and industrial Pharmacy, vol. 20, issue 1, abstract.*
Co-pending U.S. Appl. No. 10/923,021, inventors Ahmed, S., et al., filed Aug. 23, 2004 (Not Published).
Co-pending U.S. Appl. No. 11/048,120, inventors Ahmed, S., et al., filed Feb. 2, 2005 (Not Published).
Bi, Y.X., et al., "Evaluation of rapidly disintegrating tablets prepared by a direct compression method," *Drug Dev. Ind. Pharm.* 25:571-581, Marcel Dekker, Inc. (1999).
Bi, Y.X., et al., "Preparation and evaluation of a compressed tablet rapidly disintegrating in the oral Cavity," *Chem. Pharm. Bull.* 44:2121-2127, Pharmaceutical Society of Japan (1996).

(Continued)

*Primary Examiner*—Sreeni Padmanabhan
*Assistant Examiner*—Kendra D Carter
(74) *Attorney, Agent, or Firm*—Florek & Endres PLLC

(57) ABSTRACT

A non-effervescent, solid dosage form containing mirtazapine, which is used to form mirtazapine pharmaceutical tablets. The dosage form contains mirtazapine, a hydrophilic component, and at least one lubricant. In some embodiments, the dosage forms contain a salivating agent. Processes for producing mirtazapine orally disintegrating tablets are also provided.

4 Claims, 5 Drawing Sheets

U.S. PATENT DOCUMENTS

| | | |
|---|---|---|
| 2003/0165566 A1 | 9/2003 | O'Toole et al. |
| 2003/0170309 A1 | 9/2003 | Babcock et al. |
| 2003/0224043 A1 | 12/2003 | Appel et al. |
| 2003/0228358 A1 | 12/2003 | Perlman et al. |
| 2003/0229027 A1 | 12/2003 | Eissens et al. |
| 2004/0028729 A1 | 2/2004 | Shojaei et al. |
| 2004/0033258 A1 | 2/2004 | Koike |
| 2004/0058896 A1 | 3/2004 | Dietrich et al. |
| 2004/0097509 A1 | 5/2004 | Andrews et al. |
| 2004/0122106 A1 * | 6/2004 | Ohta et al. ............... 514/630 |
| 2004/0138263 A1 | 7/2004 | D'Angio et al. |
| 2004/0142034 A1 | 7/2004 | Thor et al. |
| 2005/0013857 A1 | 1/2005 | Fu et al. |
| 2005/0208141 A1 | 9/2005 | Farber et al. |

FOREIGN PATENT DOCUMENTS

| | | |
|---|---|---|
| EP | 1161941 A1 * | 12/2001 |
| EP | 1203580 A1 * | 5/2002 |
| WO | WO 8705804 A1 * | 10/1987 |
| WO | WO 98/53798 | 12/1998 |
| WO | WO 9853798 A1 * | 12/1998 |
| WO | WO 0269933 A1 * | 9/2002 |
| WO | WO 03072084 A1 * | 9/2003 |

OTHER PUBLICATIONS

Davidson, N., et al., "Comparison of an orally disintegrating ondansetron tablet with the conventional ondansetron tablet for cyclophosphamide-induced emesis in cancer patients: A multi-center, double-masked study," *Clin. Ther.* 21:492-502, Elsevier Science, Inc. (1999).

El-Arini, S.K. and Clas, S.D., "Evaluation of disintegration testing of different fast dissolving tablets using the texture analyzer," *Pharm. Dev. Technol.* 7:361-371, Marcel Dekker, Inc. (Aug. 2002).

Gan, T.J., et al., "Ondansetron orally disintegrating tablet versus placebo for the prevention of postdischarge nausea and vomiting after ambulatory surgery," *Anesth. Analg.* 94:1199-1200, International Anesthesia Research Society (Nov. 2002).

Habib, W., et al., "Fast-dissolve drug delivery systems," *Critical Reviews™ in Therapeutic Drug Carrier Systems* 17:61-72, Begell House, Inc. (2000).

Hom, F.S. and Miskel, J.J., "Enhanced dissolution rates for a series of drugs as a function of dosage form design," *Intl. J. Law Sci.* 8:18-26, International Academy of Law and Science (1971).

Ishikawa, T., et al., "Preparation of rapidly disintegrating tablet using new types of microcrystalline cellulose (PH-M Series) and low substituted-hydroxypropylcellulose or spherical sugar granules by direct compression method," *Chem. Pharm. Bull.* 49:134-139, Pharmaceutical Society of Japan (2001).

Koizumi, K., et al., "New method of preparing high-porosity rapidly saliva soluble compressed tablets using mannitol with camphor, a subliming material," *Intl. J. Pharm.* 152:127-131, Elsevier Science B.V. (1997).

LeBourgeois, J.P., et al., "Efficacy of an ondansetron orally disintegrating tablet: A novel oral formulation of this 5-HT$_3$ receptor antagonist in the treatment of fractionated radiotherapy-induced nausea and emesis," *Clin. Oncol.* 11:340-347, The Royal College of Radiologists (1999).

Lehoczky, O., et al., "Freeze dried ondansetron: first observations with the fast dissolving oral antiemetic Zofran™ Zydis™ for the prophylaxis of the cisplatin-induced emesis in gynecological cancer patients," *Neoplasma* 49:126-128, Cancer Research Institute of the Slovak Academy of Sciences (2002).

Liang, A.C. and Chen, L.H., "Fast-dissolving intraoral drug delivery systems," *Expert Opinion on Therapeutic Patents* 11:981-986, Ashley Publications Ltd. (2001).

Lowenthal, W., "Mechanism of action of tablet disintegrants," *Pharmaceutica Acta Helvetiae* 48:589-609, Elsevier B.V. (1973).

Massimo, G., et al., "Disintegration propensity of tablets evaluated by means of disintegrating force kinetics," *Pharm. Dev. Technol.* 5:163-169, Marcel Dekker, Inc. (2000).

Nakagami, H. and Nada, M., "The use of micronized cellulose disintegrants as insoluble swellable matrices for sustained-release tablets," *Drug Design and Delivery* 7:321-332, Harwood Academic Publishers GmbH (1991).

Sastry, S.V., et al., "Recent technological advances in oral drug delivery—a review," *Pharm. Sci. Technol. Today* 3:138-145, Elsevier Science (2000).

Watanabe. Y., et al., "New compressed tablet rapidly disintegrating in saliva in the mouth using crystalline cellulose and a disintegrant," *Biol. Pharm. Bull.* 18:1308-1310, Pharmaceutical Society of Japan (1995).

* cited by examiner

MIRTAZAPINE SOLID DOSAGE FORMS

The application claims the benefit of U.S. Provisional Application No. 60/491,279, filed Jul. 31, 2003, which is herein incorporated by reference in its entirety.

BACKGROUND OF THE INVENTION

1. Field of the Invention

The present invention is generally related to solid dosage forms of mirtazapine for the treatment of depression and other neurological disorders and diseases.

2. Related Art

Mirtazapine is the common name of the isomeric compound 1, 2, 3, 4, 10, 14β-hexahydro-2-methylpyrazino[2,1-a] pyrido [2,3-c] benzazepine. The use of mirtazapine is well known for the treatment of depression and the symptoms associated with depression including, memory loss, changes in mood, insomnia, lethargy, increase or decrease in weight, and anxiety.

Mirtazapine treats depression by antagonizing the adrenergic 5-HT2A, 5-HT3, and alpha 2 autoreceptors and alpha 2-heteroreceptors, and enhancing the release of norepinephrine and 5-HT1A-mediated serotonergic transmission. It is not known exactly how mirtazapine accomplishes this function. It is also being considered for the treatment of psychotic disorders and diseases such as schizophrenia and movement disorders such as Parkinson's tremors, as disclosed in U.S. Pat. No. 6,281,207. Mirtazapine can be administered alone or with other pharmaceuticals such as selective serotonin reuptake inhibitors (SSRIs), such as those described in U.S. Pat. No. 5,977,099, or antipsychotic agents, such as those described in U.S. Pat. No. 6,150,353.

Mirtazapine has been found to have limited drug interaction and few side effects associated with many antidepressants such as sexual dysfunction. The tetracylic compound is currently manufactured through the methods described in U.S. Pat. No. 4,062,848, forming a racemic mixture of isomeric compounds.

Oral administration in the form of a conventional tablet, pill or capsule constitutes the generally preferred route for administration of pharmaceuticals, such as mirtazapine, since this route is generally convenient and acceptable to patients. Unfortunately such compositions may be associated with certain disadvantages, particularly in the treatment of pediatric or geriatric patients, who may dislike or have difficulty in swallowing such compositions, or where administration of a conventional tablet, pill or capsule is not feasible. It is highly desirable, particularly in the treatment of acute conditions, that pharmaceutical compositions have a rapid and consistent onset of action combined with sustained activity and good bioavailability.

Since a solid preparation such as an oral tablet requires water for swallowing, a liquid dosage form is normally preferred for the elderly, infants or patients who have difficulty in swallowing. However, a liquid preparation has shortcomings regarding difficulties in handling, especially in measuring an accurate dosage, and that it is not suitable for drugs which are unstable in a moist environment. Thus, an effort has been made to develop a rapidly disintegrating tablet of drugs which can easily disintegrate by the action of saliva.

For example, oral dosage forms have been developed including effervescents which rapidly disintegrate in the mouth and provide taste-masking. See Wehling et al., U.S. Pat. No. 5,178,878. These dosage forms provide significant problems in terms of production, storage, transport and during consumer usage. They are also significantly more costly to produce than conventional tablets.

U.S. Pat. No. 5,178,878 discloses an effervescent tablet which comprises microparticles of various active ingredients. Effervescence is typically created by the formation of gas bubbles upon a reaction of an alkali metal carbonate or carbonate source with an acid or an acid source. The effervescence aids in the complete disintegration of the tablet upon oral administration.

Mirtazapine is currently available in an effervescent oral disintegrating tablet. However, effervescent tablets containing an alkalizing agent are usually moisture sensitive, may be incompatible with an acidic drug and require protection due to their sensitivity to humidity. In addition, the manufacture of effervescent tablets requires strict humidity controls.

Therefore, there is a need for an orally disintegrating tablet of a pharmaceutical composition that does not require an alkalizing agent such as a carbonate or bicarbonate; is compatible with an acidic drug; is physically stable under humid conditions; and is easier to manufacture.

SUMMARY OF THE INVENTION

In some embodiments, the invention provides a non-effervescent, solid dosage form adapted for oral administration to a mammal:

about 1 to about 60% by weight of mirtazapine;

about 1 to about 95% by weight of a hydrophilic component selected from the group consisting of a water-soluble component, a water-insoluble component, or combinations thereof, wherein the water-soluble component is selected from the group consisting of cellulose derivatives, polyol, water-soluble carbohydrate, a component having a —CHOH group, hydroxypropyl cellulose, methyl cellulose, hydroxypropyl methyl cellulose, polyvinyl pyrrolidone, a component having a —CHCOOH group, tartaric acid, citric acid, malic acid, succinic acid, sodium and potassium salts thereof, or combinations thereof, wherein the water-soluble carbohydrate is selected from the group consisting of mannitol, xylitol, sorbitol, malitol, lacitol, erytritol, xylose, arabinose, pentose, galactose, dextrose, inositol, sucrose, trehalose, or combinations thereof, and wherein the water-insoluble component is selected from the group consisting of microcrystalline cellulose, crospovidone, croscarmelose sodium, sodium starch glycolate, AMBERLITE (Rohm and Haas, Philadelphia, Pa.), calcium silicate, calcium trisilicate, magnesium silicate, magnesium trisilicate, modified starches, or combinations thereof;

up to about 5% by weight of at least one lubricant selected from the group consisting of magnesium stearate, sodium stearyl fumarate, calcium stearate, sodium stearate, stearic acid, talc, hydrogenated vegetable oil, aluminum stearate, silica gel, colloidal silicon dioxide, or combinations thereof;

wherein said dosage form does not rely upon effervescence for disintegration of said dosage form;

wherein dissolution of said dosage form in a medium of 900 mL of 0.1 N HCl with a paddle speed of 50 rpm is greater than about 75% at five minutes; and wherein the water-soluble and water-insoluble component are provided in a weight ratio from about 20:80 to about 95:5.

In some embodiments, the solid dosage form further comprises about 0.1 to about 30% by weight of at least one salivating agent selected from the group consisting of mannitol, xylitol, tartaric acid, citric acid, malic acid, fumaric acid, adipic acid, succinic acid, sodium and potassium salts thereof, and combinations thereof.

In some embodiments, the dosage form further comprises, about 1 to about 50% of a first hydrophilic component selected from a group consisting of cellulose derivatives, hydrophilic polymers, polyvinyl pyrrolidone, and combinations thereof. In some embodiments, the first hydrophilic component is selected from the group consisting of microcrystalline cellulose, hydroxypropyl cellulose, methyl cellulose, hydroxypropyl methyl cellulose, polyvinyl pyrrolidone, and combinations thereof.

In some embodiments the dosage form comprises a component having a negative heat of solution, the component selected from the group consisting of mannitol, xylitol, sorbitol, sucrose, and combinations thereof.

The solid dosage forms of the present invention do not rely upon effervescence for release of the active agent since the present dosage forms lack the base necessary for the effervescent-causing reaction, i.e. the release of bicarbonate. In some embodiments, the solid dosage forms of the present invention have a have a dissolution of greater than 75% in five mins in a medium of 900 mL of 0.1 N HCl with a paddle speed of 50 rpm. In some embodiments, the solid dosage forms of the present invention have a have a dissolution of greater than 95% in five mins in a medium of 900 mL of 0.01 N HCl with a paddle speed of 50 rpm.

In some embodiments, the invention provides a process of making a non-effervescent, solid dosage form adapted for oral administration which comprises:

a) mixing about 1 to about 60% by weight of mirtazapine; about 1 to about 95% by weight of a hydrophilic component selected from the group consisting of a water-soluble component, a water-insoluble component, or combinations thereof, wherein the water-soluble component is selected from the group consisting of cellulose derivatives, polyol, a component having a —CHOH group, water-soluble carbohydrate, hydroxypropyl cellulose, methyl cellulose, hydroxypropyl methyl cellulose, polyvinyl pyrrolidone, a component having a —CHCOOH group, tartaric acid, citric acid, malic acid, succinic acid, sodium and potassium salts thereof, and combinations thereof, wherein the water-soluble carbohydrate is selected from the group consisting of mannitol, xylitol, sorbitol, malitol, lacitol, erytritol, xylose, arabinose, pentose, galactose, dextrose, inositol, sucrose, trehalose, and combinations thereof, and wherein the water-insoluble component is selected from the group consisting of microcrystalline cellulose, crospovidone, croscarmelose sodium, sodium starch glycolate, AMBERLITE, calcium silicate, calcium trisilicate, magnesium silicate, magnesium trisilicate, modified starches, and combinations thereof; and up to about 5% by weight of at least one lubricant selected from the group consisting of magnesium stearate, sodium stearyl fumarate, calcium stearate, sodium stearate, stearic acid, talc, hydrogenated vegetable oil, aluminum stearate, silica gel, colloidal silicon dioxide, and combinations thereof in an agitator to form a mixture;

b) followed by directly compressing the mixture to form a pharmaceutical tablet, wherein said tablet does not rely upon effervescence for disintegration of said tablet, wherein dissolution of said dosage form in a medium of 900 mL of 0.1 N HCl with a paddle speed of 50 rpm is greater than about 75% at five minutes, and wherein the water-soluble and water-insoluble component are provided in a weight ratio from about 20:80 to about 95:5.

In some embodiments, the process further comprises mixing, about 1 to about 50% of a first hydrophilic component selected from a group consisting of cellulose derivatives, hydrophilic polymers, polyvinyl pyrrolidone, and combinations thereof. In some embodiments, the first hydrophilic component is selected from the group consisting of microcrystalline cellulose, hydroxypropyl cellulose, methyl cellulose, hydroxypropyl methyl cellulose, polyvinyl pyrrolidone, and combinations thereof.

Pharmaceutical tablets formed from this process are also provided by the present invention. The solid dosage forms of the present invention do not rely upon effervescence for release of the active agent since the present dosage forms lack the base necessary for the effervescent-causing reaction, i.e. the release of bicarbonate. In some embodiments, the solid dosage forms of the present invention have a have a dissolution of greater than 75% in five mins in a medium of 900 mL of 0.1 N HCl with a paddle speed of 50 rpm. In some embodiments, the solid dosage forms of the present invention have a have a dissolution of greater than 95% in five mins in a medium of 900 mL of 0.01 N HCl with a paddle speed of 50 rpm.

In some embodiments, the invention provides a method of treating neurological disorders and diseases including depression, symptoms associated with depression including suicidal thoughts, drowsiness, memory loss, anxiety, sleeplessness and others, psychotic disorders and diseases such as schizophrenia and movement disorders and diseases in a human which comprises administering the solid dosage form of the present invention to a mammal in need thereof.

Particularly, the present invention provides for mirtazapine orally disintegrating tablets which do not rely upon effervescence for release of the active agent. The non-effervescent, mirtazapine tablets have various advantages over effervescent tablets. For example, the present dosage form does not require an alkalizing agent such as a carbonate or bicarbonate; a non-effervescent, tablet is compatible with an acidic drug; the present pharmaceutical tablet is more physically stable, less sensitive to humidity, and thus are easier to package since they need not be protected from moisture at all times; and the manufacture of the present pharmaceutical tablets does not require the strict humidity controls that effervescent tablets typically do.

In some embodiments, the hardness of the non-effervescent, solid dosage forms is about 0.1 to about 5 kp. In some embodiments, the hardness of the dosage forms is about 0.1 to about 3 kp. In some embodiments, the hardness of the dosage forms is greater than about 1.0 kp after exposure for 24 hours at 25° C. and 60% relative humidity, and is greater than about 0.8 kp after exposure for 60 minutes at 40° C. and 75% relative humidity.

In some embodiments the invention provides a non-effervescent, solid dosage form, wherein the dosage form having a first hardness being the dosage form inside a closed space, wherein the dosage form having a second hardness being the dosage form exposed to about 25° C. and about 60% relative humidity for about 24 hours, and wherein the second hardness is at least about 50% of the first hardness. In some embodiments, the invention provides, a non-effervescent, solid dosage form, wherein the dosage form having a first hardness being the dosage form inside a closed space, wherein the dosage form having a second hardness being the dosage form exposed to about 40° C. and about 75% relative humidity for about 15 minutes, and wherein the second hardness is at least about 50% of the first hardness.

Thus, an orally disintegrating tablet of a mirtazapine pharmaceutical composition is provided which does not require an alkalizing agent such as a carbonate or bicarbonate; is compatible with an acidic drug; is physically stable under humid conditions; and is easier to manufacture. The mirtazapine dosage form of the present invention provides orally disintegrating tablets having a high tolerance of humidity; maintain their physical integrity when exposed to environmental conditions thus facilitating processing, compressing and packaging; are more stable under harsh conditions; and last longer when removed from packaging as compared to reference mirtazapine tablets.

DETAILED DESCRIPTION OF THE INVENTION

Figure 1:
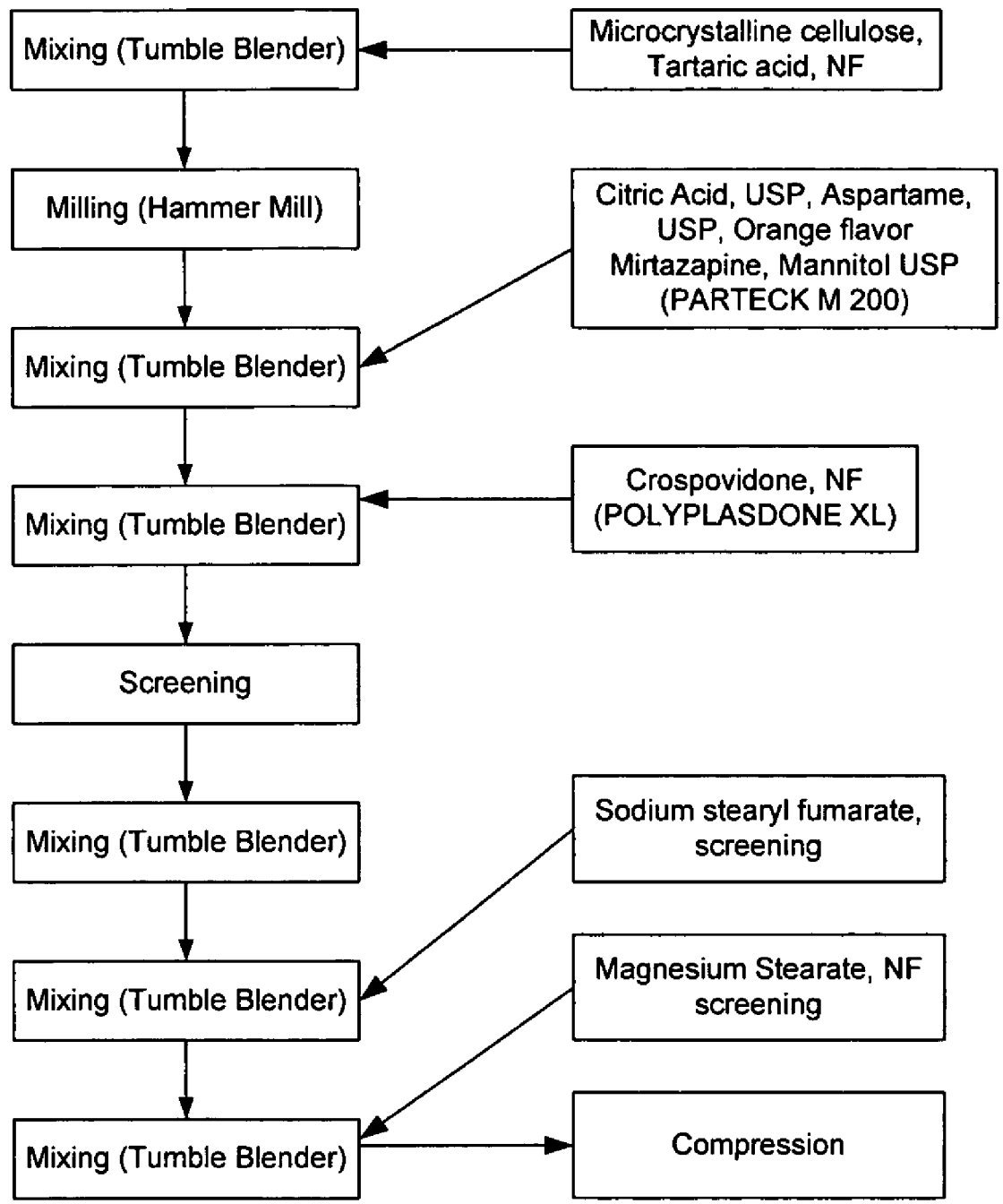
FIG. 1 is a flow chart illustrating a dry-mixing process of making some of the mirtazapine formulations according to the present invention.

Throughout the present document, all expressions of percentage, ratio, and the like, will be in weight units unless otherwise indicated.

The present invention contemplates solid oral dosage forms, such as a pharmaceutical tablet containing mirtazapine. The dosage forms of the present invention do not rely upon effervescence for release of the active agent. The mirtazapine formulations contemplated can employ a racemic mixture of mirtazapine or an enantiomeric excess of, or a substantially pure enantiomer, i.e., R-mirtazapine and S-mirtazapine. See U.S. Pat. No. 4,062,848. As will be appreciated by those skilled in the art, salts, hydrates, solvates, and the like, could be employed in the present invention to obtain the same beneficial effects as that provided by the base form mirtazapine. Accordingly, as used herein, the term "mirtazapine" contemplates all such forms, with a racemic mixture of mirtazapine being preferred.

As used herein, the term "pharmaceutically effective" refers to that amount of mirtazapine, which diminishes one or more symptoms of the disease or disorder being treated. For example, a pharmaceutically effective amount for the treatment of depression refers to the amount which when administered diminishes one or more symptoms of depression, such as insomnia or anxiety. The precise therapeutic dosage of mirtazapine necessary to be pharmaceutically active will vary with age, size, sex and condition of the subject, the nature and severity of the disorder or disease to be treated, and the like; thus, a precise pharmaceutically effective amount cannot be specified in advance and will be determined by a caregiver. However, appropriate amounts can be determined by routine experimentation with animal models. In general terms, an effective daily dose is about 5 to 50 milligrams (mg) per day per human subject of mirtazapine. In some embodiments, an effective daily dose is about 5 mg per day. In some embodiments, an effective daily dose is about 10 mg per day. In some embodiments, an effective daily dose is about 15 mg per day. In some embodiments, an effective daily dose is about 30 mg per day. In some embodiments, an effective daily dose is about 45 mg per day.

The term "tablet" as used herein is intended to encompass compressed pharmaceutical dosage formulations of all shapes and sizes, whether coated or uncoated.

As used herein, the term "excipient" refers to the additives used to convert an active compound into a form suitable for its intended purpose. For dosage forms of the present invention suitable for administration to humans, the term "excipient" is meant to include, but is not limited to, those ingredients described in *Remington: The Science and Practice of Pharmacy*, Lippincott Williams & Wilkins, 21$^{st}$ ed. (2004), which is herein incorporated by reference in its entirety.

As used herein, the term "disintegration" refers to the loss of integrity of the dosage forms of the invention to form granules or aggregates or particles, as generally described in *Remington: The Science and Practice of Pharmacy*, Lippincott Williams & Wilkins, 21$^{st}$ ed. (2004).

As used herein, "dissolution" refers to the process by which mirtazapine goes into solution from the solid dosage forms of the invention.

As used herein, a "closed space" refers to the space within a package or container such as a blister pack or foil-wrapped package containing the solid dosage forms of the invention.

As used herein, "low humidity" refers to the conditions provided by use of desiccated bags to control moisture or to conditions inside a package such as a blister pack containing the solid dosage forms of the invention.

In some embodiments, the invention provides a non-effervescent, solid dosage form adapted for oral administration to a mammal:

about 1 to about 60% by weight of mirtazapine;

about 1 to about 95% by weight of a hydrophilic component selected from the group consisting of a water-soluble component, a water-insoluble component, or combinations thereof, wherein the water-soluble component is selected from the group consisting of cellulose derivatives, polyol, water-soluble carbohydrate, a component having a —CHOH group, hydroxypropyl cellulose, methyl cellulose, hydroxypropyl methyl cellulose, polyvinyl pyrrolidone, a component having a —CHCOOH group, tartaric acid, citric acid, malic acid, succinic acid, sodium and potassium salts thereof, or combinations thereof, wherein the water-soluble carbohydrate is selected from the group consisting of mannitol, xylitol, sorbitol, malitol, lacitol, erytritol, xylose, arabinose, pentose, galactose, dextrose, inositol, sucrose, trehalose, or combinations thereof, and wherein the water-insoluble component is selected from the group consisting of microcrystalline cellulose, crospovidone, croscarmelose sodium, sodium starch glycolate, AMBERLITE (Rohm and Haas, Philadelphia, Pa.), calcium silicate, calcium trisilicate, magnesium silicate, magnesium trisilicate, modified starches, or combinations thereof;

up to about 5% by weight of at least one lubricant selected from the group consisting of magnesium stearate, sodium stearyl fumarate, calcium stearate, sodium stearate, stearic acid, talc, hydrogenated vegetable oil, aluminum stearate, silica gel, colloidal silicon dioxide, or combinations thereof;

wherein said dosage form does not rely upon effervescence for disintegration of said dosage form;

wherein dissolution of said dosage form in a medium of 900 mL of 0.1 N HCl with a paddle speed of 50 rpm is greater than about 75% at five minutes; and wherein the water-soluble and water-insoluble component are provided in a weight ratio from about 20:80 to about 95:5. In some embodiments, the dissolution of the dosage form in a medium of 900 mL of 0.01 N HCl with a paddle speed of 50 rpm is greater than about 95% at five minutes.

In some embodiments, the dosage form further comprises about 0.1 to about 30% by weight of at least one salivating agent selected from mannitol, tartaric acid, citric acid, malic acid, fumaric acid, adipic acid, succinic acid, sodium and potassium salts thereof, and combinations thereof.

In some embodiments, the dosage form further comprises, about 1 to about 50% of a first hydrophilic component selected from a group consisting of cellulose derivatives, hydrophilic polymers, polyvinyl pyrrolidone, and combinations thereof. In some embodiments, the first hydrophilic component is selected from the group consisting of microcrystalline cellulose, hydroxypropyl cellulose, methyl cellulose, hydroxypropyl methyl cellulose, polyvinyl pyrrolidone, and combinations thereof.

The dosage forms of the present invention do not rely upon effervescence for release of the active agent, need not contain an alkalyzing agent, but can contain any other additives, colorings and/or flavorings that are pharmaceutically acceptable. In some embodiments, the dissolution rate of dosage forms of the present invention, in a medium of 900 mL of 0.01 N HCl with a paddle speed of 50 rpm, is greater than 95% at five minutes.

In some embodiments, the dosage form comprises about 0.5 to about 40% mirtazapine, up to about 30% of at least one salivating agent, about 5 to about 50% of a first hydrophilic component, about 10 to about 80% of a water-soluble carbohydrate, about 10 to about 50% of a disintegrating agent, and less than about 5% of at least one lubricant.

In some embodiments, the dosage form comprises about 0.5 to about 10% by weight of mirtazapine; up to about 10% by weight of at least one salivating agent; about 5 to about 15% by weight of a first hydrophilic component; about 35 to about 65% by weight of a water-soluble carbohydrate; about 15 to about 35% by weight of a disintegrating agent; and about 0.5 to about 4% by weight of at least one lubricant.

In some embodiments, the dosage form comprises about 6% mirtazapine, about 14.4% of one or more salivating agents, about 6% of a first hydrophilic component, about 44% of a water-soluble carbohydrate, about 24% of a disintegrating agent, and about 1.4% of at least two lubricants.

The present invention contemplates the use of at least one salivating agent source suitable for human consumption. Salivating agents include organic compounds such as polyols and mild acids. Examples of water-soluble carbohydrates and polyols which can be used as salivating agents in the present invention are xylitol and mannitol. Mild acids are used to adjust the pH, or acidity, of the pharmaceutical composition and in some cases to provide flavoring. A purpose of using a mild acid in the present composition is to provide for a sour taste to stimulate saliva secretion, which helps disintegrate the tablets. Acceptable mild acids are tartaric acid, citric acid, malic acid, fumaric acid, adipic acid, succinic acid, sodium and potassium salts thereof, and combinations thereof. Also contemplated is the use of acid anhydrides and acid salts such as sodium dihydrogen phosphate, disodium dihydrogen pyrophosphate, acid citrate salts, and sodium acid sulfite. It is preferred that either tartaric acid, citric acid, or both, or sodium or potassium salts thereof, or combinations thereof are used in the present formulation. Most preferred is a combination of tartaric acid, NF and citric acid USP Anhydrous Powder.

Preferred water-soluble carbohydrates for use in the present invention include but are not limited to mannitol, xylitol, sorbitol, malitol, lacitol, erytritol, xylose, arabinose, pentose, galactose, dextrose, inositol, sucrose, trehalose and mixtures thereof, most preferably, mannitol USP available under the trade name PARTECK M-200 (Merck KGaA, Darmstadt, Germany).

In some embodiments, the invention provides a solid dosage form which further comprises a component having a negative heat of solution selected from the group consisting of mannitol, xylitol, sorbitol, sucrose, and combinations thereof.

The mirtazapine dosage form of the present invention neither relies upon effervescence for release of the active agent nor aids in its complete disintegration. Instead, the present invention employs a disintegrating agent. Particularly useful disintegrating agents are super-disintegrating agents such as crospovidone, croscarmelose sodium, AMBERLITE (Rohm and Haas, Philadelphia, Pa.), and sodium starch glycolate. The preferred disintegrating agent is crospovidone, NF available under the trade name POLYPLASDONE XL (ISP Technologies, Wayne, N.J.). Microcrystalline cellulose also aids in disintegration by acting as a wicking agent. Wicking agents take moisture from the ambient conditions and draws it into the tablet to aid in dissolving the water soluble components. Types of AMBERLITE (Rohm and Haas, Philadelphia, Pa.) resins for use in the formulation include but are not limited to AMBERLITE IRP64, AMBERLITE IRP69, AMBERLITE IRP88, and combinations thereof. The components of the present invention are sufficient for complete disintegration without the use of effervescent agents. In some embodiments, the dosage form further comprises an agent selected from the group consisting of calcium silicate, magnesium silicate, magnesium trisilicate, and combinations thereof. While not wishing to be bound by a specific theory, it appears that the agent, such as, calcium silicate, calcium trisilicate, magnesium trisilicate, magnesium silicate, and combinations thereof, might act by facilitating the disintegration action of the disintegrating agents such as crospovidone. In some embodiments, the weight ratio of the disintegrating agents such as crospovidone to that of agents such as calcium silicate can range from 9:1 to 1:9.

The present invention contemplates the use of at least one lubricant to assist in the removal of tablets from the dies during tablet compression and to reduce the friction of particles. Common hydrophobic lubricants suitable in the present formulation are: magnesium stearate, sodium stearyl fumarate, calcium stearate, sodium stearate, stearic acid, talc, hydrogenated vegetable oil, aluminum stearate, silica gel, such as colloidal silicon dioxide, and mixtures thereof. The presence of at least one of the above mentioned lubricants is contemplated in the present invention. Preferred is a combination of magnesium stearate, NF and sodium stearyl fumarate, NF. Sodium stearyl fumarate is commonly available under the tradename PRUV (Penwest Pharmaceuticals Co., Patterson, N.Y.).

In addition to the above mentioned ingredients, other excipients can be added to the present composition. In particular, coloring agents and flavoring agents can be added. Any coloring suitable for oral ingestion, including natural synthetic coloring such as F.D.& C. dyes, are appropriate in the present invention. A natural or an artificial sweetener can be employed to improve the taste of the tablet upon disintegration, such as aspartame, sucralose, acesulfame potassium, sodium cyclamate, saccharin and the like. In some embodiments, the sweetener is aspartame. In addition, natural and artificial flavorings can be added. The citrus flavorings, including but not limited to orange, tangerine, lemon, lime, lemon-lime, citrus, and the like, are particularly suited to combat the bitter taste of mirtazapine. In some embodiments, orange flavor is preferred. In some embodiments, strawberry flavor is preferred.

The pharmaceutical dosage forms of the present invention are useful in the therapeutic treatment for patients suffering from DSM-IV diagnosable disorders such as schizophrenia, Alzheimer's Disease, autism, depression, benign forgetfulness, childhood learning disorders, close head injury, and attention deficit disorder. See U.S. Pat. No. 6,228,875. In addition, the mirtazapine of the present invention can be used in treating movement disorders such as Parkinsonian tremors, rubral tremors, post-traumatic tremors, drug-induced tremors (e.g. induced by lithium or other drug agents), cerebellar tremors associated with lesions of the cerebellum or cerebellar outflow pathway, Tourette's syndrome tremors and other peripheral neuropathy-associated tremors, akathisias, asterixis, athetosis, choreaathetosis, tics, chorea/choreaform movements, dystonias, spasticity, restless legs syndrome, hyperkinetic movement disorders, hemiballismus, myoclonus, tardive dyskinesia and other types of dyskinesia, and sleep apnea disorders. See U.S. Pat. Nos. 6,281,207 and 6,303,595.

In addition, the mirtazapine dosage form can be used to treat other mental disorders and diseases currently being treated by antidepressants, such as, but not limited to, selective serotonin reuptake inhibitors (SSRIs) such as depression (including major depression (single episode, recurrent, melancholic), atypical, dysthymia, subsyndromal, agitated, retarded, co-morbid with cancer, diabetes, or post-myocardial infarction, involutional, bipolar disorder, psychotic depression, endogenous, and reactive, obsessive-compulsive disorder, bulimia. In addition, the formulations can be used to treat people suffering from pain (given alone or in combination with other pain relievers), obsessive-compulsive personality disorder, post-traumatic stress disorder, hypertension, atherosclerosis, anxiety, anorexia nervosa, panic, social phobia, stuttering, sleep disorder, weight loss, agoraphobia, improving memory, amnesia, smoking cessation, nicotine withdrawal syndrome symptoms, disturbance of mood and/or appetite associated with pre-menstrual syndrome, depressed mood and/or carbohydrate craving associated with pre-menstrual syndrome, disturbance of mood, disturbance of appetite or disturbances which contribute to recidivism associated with nicotine withdrawal, circadian rhythm disorder, borderline personality disorder, hypochondriasis, pre-menstrual syndrome (PMS), late luteal phase dysphoric disorder, pre-menstrual dysphoric disorder, trichotillomania, symptoms following discontinuation of other antidepressants, aggressive/intermittent explosive disorder, compulsive gambling, compulsive spending, compulsive sex, psychoactive substance abuse disorder, sexual disorder, schizophrenia, premature ejaculation, or psychiatric symptoms such as stress, worry, anger, rejection sensitivity, and lack of mental or physical energy. See e.g., U.S. Pat. No. 6,150,353.

In some embodiments, the invention provides a process for preparing a pharmaceutical tablet, the process comprising:

In some embodiments, the invention provides a process of making a non-effervescent, solid dosage form adapted for oral administration which comprises:

a) mixing about 1 to about 60% by weight of mirtazapine; about 1 to about 95% by weight of a hydrophilic component selected from the group consisting of a water-soluble component, a water-insoluble component, or combinations thereof, wherein the water-soluble component is selected from the group consisting of cellulose derivatives, polyol, a component having a —CHOH group, water-soluble carbohydrate, hydroxypropyl cellulose, methyl cellulose, hydroxypropyl methyl cellulose, polyvinyl pyrrolidone, wherein the water-soluble carbohydrate is selected from the group consisting of mannitol, xylitol, sorbitol, malitol, lacitol, erytritol, xylose, arabinose, pentose, galactose, dextrose, inositol, sucrose, trehalose, and combinations thereof, a component having a —CHCOOH group, tartaric acid, citric acid, malic acid, succinic acid, sodium and potassium salts thereof, and combinations thereof, and wherein the water-insoluble component is selected from the group consisting of microcrystalline cellulose, crospovidone, croscarmelose sodium, sodium starch glycolate, AMBERLITE, calcium silicate, calcium trisilicate, magnesium silicate, magnesium trisilicate, modified starches, and combinations thereof; and up to about 5% by weight of at least one lubricant selected from the group consisting of magnesium stearate, sodium stearyl fumarate, calcium stearate, sodium stearate, stearic acid, talc, hydrogenated vegetable oil, aluminum stearate, silica gel, colloidal silicon dioxide, and combinations thereof in an agitator to form a mixture;

b) followed by directly compressing the mixture to form a pharmaceutical tablet, wherein said tablet does not rely upon effervescence for disintegration of said tablet, wherein dissolution of said dosage form in a medium of 900 mL of 0.1 N HCl with a paddle speed of 50 rpm is greater than about 75% at five minutes, and wherein the water-soluble and water-insoluble component are provided in a weight ratio from about 20:80 to about 95:5. In some embodiments, the dissolution of the dosage form in a medium of 900 mL of 0.01 N HCl with a paddle speed of 50 rpm is greater than about 95% at five minutes.

In some embodiments, the process further comprises mixing, about 1 to about 50% of a first hydrophilic component selected from a group consisting of cellulose derivatives, hydrophilic polymers, polyvinyl pyrrolidone, and combinations thereof. In some embodiments, the first hydrophilic component is selected from the group consisting of microcrystalline cellulose, hydroxypropyl cellulose, methyl cellulose, hydroxypropyl methyl cellulose, polyvinyl pyrrolidone, and combinations thereof.

The non-effervescent, solid dosage forms formed from the present process have a hardness of from about 0.1 to about 5 kp. In some embodiments, the hardness of the dosage forms can be 0.1 to about 3 kp. In some embodiments, the hardness of the dosage forms is greater than about 1.0 kp after exposure for 24 hours at 25° C. and 60% relative humidity, and is greater than about 0.8 kp after exposure for 60 minutes at 40° C. and 75% relative humidity.

When the solid dosage forms of the invention such as the tablets come off a tablet press, they are kept under low humidity conditions by use of, e.g., desiccated bags to control the moisture around the tablets. The tablets stored under desiccated conditions are then packaged into blister packs under ambient controlled conditions at temperatures of about 25° C. and relative humidity ranging from about 35% to about 60% relative humidity, which results in a decrease in hardness of the tablet ranging from about 0.1 to about 0.5 kp. While not wishing to be bound by any specific theory, it is believed that because a low amount of air is trapped inside a blister pack and around a packaged tablet, the relative humidity of the atmosphere around a tablet inside a blister pack is low. Moreover, the packaging materials used for preparing the blister pack such as aluminum are impermeable to moisture and maintain the conditions of low humidity around the solid dosage forms for long periods of time.

When a user opens the package containing the solid dosage form to consume the dosage form, then the dosage form is exposed to conditions such as about 25° C. and about 60% relative humidity, or about 40° C. and about 75% relative humidity, or about 25° C. and about 35% relative humidity, or other ambient atmosphere, for periods of time whereby the hardness of the solid dosage form decreases. However, the formulation of the dosage form is such that even after exposure to conditions such as about 25° C. and about 60% relative humidity for about 24 hours, or about 40° C. and about 75% relative humidity for about 15 min, or about 25° C. and about 35% relative humidity for about 24 hours, or about 25° C. and about 35% relative humidity for about 6 hours, or about 25° C. and about 35% relative humidity for about 1 hr, the hardness of the exposed dosage form is at least about 50% of the hardness of the dosage form when packed inside a package. This physical property of the formulations of the invention whereby the dosage form retains its hardness for a period of time after its removal from a package is advantageous to users as patients do not have to consume the dosage form as soon as they open a package. In some embodiments, the package can be prepared under conditions including, but not limited to low humidity, controlled temperature, low oxygen, inert atmosphere, under nitrogen, in vacuum, and combinations thereof.

In some embodiments, the invention provides, a non-effervescent, solid dosage form, wherein the dosage form having a first hardness being the dosage form inside a closed space, wherein the dosage form having a second hardness being the dosage form exposed to about 25° C. and about 60% relative humidity for about 24 hours, and wherein the second hardness is at least about 50% of the first hardness. In some embodiments, the invention provides a non-effervescent, solid dosage form, wherein the dosage form having a first hardness being the dosage form inside a closed space, wherein the dosage form having a second hardness being the dosage form exposed to about 40° C. and about 75% relative humidity for about 15 minutes, and wherein the second hardness is at least about 50% of the first hardness.

The disintegrating tablets must be made under generally anhydrous conditions. To assist in the cohesion of dry ingredient, it is helpful to include a hydrophilic component, which includes water-soluble and water-insoluble components such as microcrystalline cellulose, hydroxypropyl cellulose, methylcellulose, hydroxypropyl methylcellulose, and polyvinyl pyrrolidone. In some embodiments, the hydrophilic component is microcrystalline cellulose, in particular, microcrystalline cellulose NF available under the trade name AVICEL PH 101 (FMC BioPolymer, Philadelphia, Pa.).

Some embodiments of the present invention are shown in Table 1.

TABLE 1

Mirtazapine Formulations

| Ingredient | % | Preferred (mg) | More Preferred/mg | Most Preferred/mg |
|---|---|---|---|---|
| Mirtazapine | 6.0 | 1 to 60 | 1 to 30 | 1 to 10 |
| Tartaric Acid | 6.0 | 0 to 20 | 0 to 15 | 0 to 10 |
| Microcrystalline Cellulose | 6.0 | 1 to 80 | 1 to 50 | 1 to 10 |
| Citric Acid | 8.4 | 0 to 20 | 0 to 15 | 0 to 10 |
| Aspartame | 4.0 | 0.1 to 10 | 1 to 8 | 1 to 5 |
| Orange Flavor | 0.6 | 0 to 2.4 | 0 to 1.2 | 0 to 0.6 |
| Mannitol | 43.6 | 0 to 80 | 0 to 60 | 0 to 50 |
| Crospovidone | 24.0 | 3 to 50 | 5 to 40 | 10 to 30 |
| Magnesium Stearate | 0.6 | 0 to 5 | 0 to 3 | 0 to 1 |

TABLE 1-continued

Mirtazapine Formulations

| Ingredient | % | Preferred (mg) | More Preferred/mg | Most Preferred/mg |
|---|---|---|---|---|
| Sodium Stearyl Fumarate | 0.8 | 0 to 5 | 0 to 3 | 0 to 1 |

A compressed tablet contemplated in the present invention has a hardness of from about 0.1 to about 5 kiloponds (kp). In some embodiments, the hardness of the tablets ranges from about 0.1 kp to about 3 kp. In some embodiments, the hardness of the tablet is about 2 kp.

FIG. 1 depicts a flow chart of a manufacturing process which can be used to form pharmaceutical tablets of the pharmaceutical composition of the present invention. Tartaric acid and microcrystalline cellulose are mixed in an agitator; citric acid, aspartame, orange flavoring, mirtazapine and mannitol are subsequently added and mixed to form a mixture; crospovidone is then transferred to the agitator and mixed in with the mixture followed by subsequent additions of sodium stearyl fumarate and magnesium stearate; the composition is mixed and the resultant mixture is compressed to form mirtazapine pharmaceutical tablets.

Figure 2:
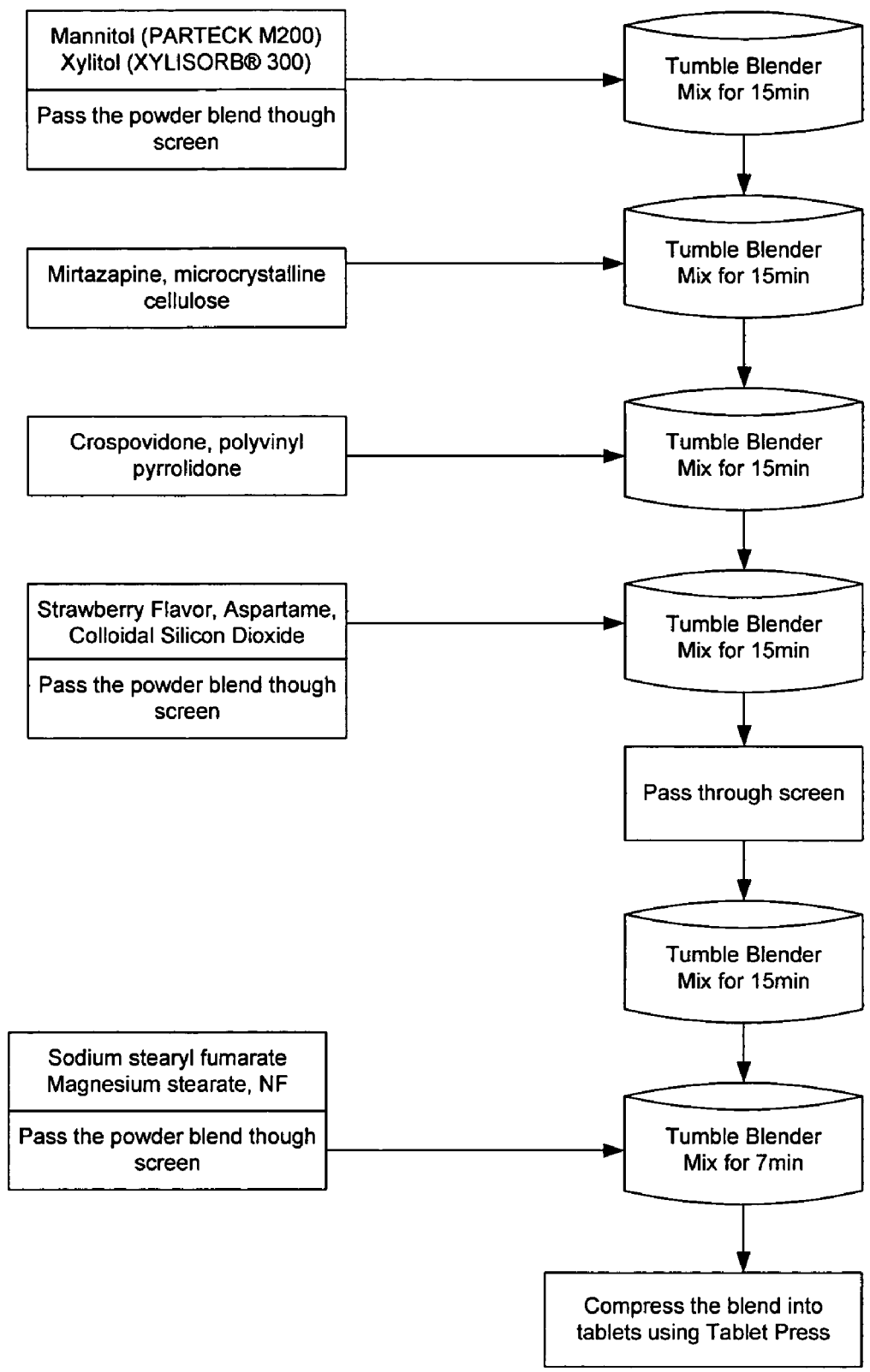
FIG. 2 is a dry-mixing process of making some of the mirtazapine formulations of the present invention.

FIG. 2 depicts a flow chart of a dry mixing process to prepare mirtazapine orally disintegrating tablets. Mannitol and xylitol are mixed and passed through a screen, and then mixed in a tumble blender, e.g., GEMCO 20 cubic feet (General Machine Company of New Jersey Inc., Middlesex, N.J.). Mirtazapine and microcrystalline cellulose are subsequently added to the tumble blender and mixed. Crospovidone and polyvinyl pyrrolidone are added to the mixture. Strawberry flavor, aspartame and colloidal silicon dioxide are passed through a screen and then added to the tumble blender and mixed with the above mixture, then passed through a screen and then again transferred to a tumble blender. Sodium stearyl fumarate and magnesium stearate are passed through a screen, e.g. Russell Finex #30 (Russel Finex Inc., Pineville, N.C.), and added to the tumble blender, mixed and then the blend is compressed into tablets using a tablet press.

The disclosed mirtazapine dosage forms can be prepared as a solid oral dosage forms, preferably as orally disintegrating tablets, for medical administration. The preferred method of administration is in the form of a non-effervescent, orally disintegrating tablet compressed from a mixture of the dry ingredients. In some embodiments, mirtazapine is in the form of uncoated mirtazapine particles. The net weight of a compressed tablet comprising the mirtazapine dosage form of the present invention is from about 50 mg to about 1000 mg. Preferably, the mirtazapine dosage form would be made commercially available in two strengths, one about 250 mg and the other about 500 mg, each containing proportional doses of mirtazapine.

It has been unexpectedly found that mirtazapine tablets formed from the present pharmaceutical dosage form are physically stable at humid conditions although they have similar dissolution profiles to that of reference mirtazapine effervescent tablets.

Moreover, the mirtazapine tablets of the present invention are easier to package because they are more physically stable, less sensitive to moisture and are thus less fragile than reference mirtazapine tablets.

While not wishing to be bound by a specific theory, it is believed that upon oral administration to a patient, the dosage forms of the invention undergo disintegration to form granules or aggregates or fine particles, and subsequently most of the mirtazapine is released into solution.

The following examples of processing conditions and parameters are given for the purpose of illustrating the present invention and shall not be construed as being limitations on the scope or spirit of the invention.

EXAMPLES

Example 1

FIG. 1 is a flow chart describing the process for making the mirtazapine formula of the present invention. Microcrystalline cellulose and tartaric acid are combined in a 20 cubic foot GEMCO blender (General Machine Company of New Jersey Inc., Middlesex, N.J.) for seven minutes with the agitator off. The mixture is then milled, e.g., through a FITZMILL (Fitzpatrick, South Plainfield, N.J.) fitted with a 1522-033 screen and a hammer forward. The mixture is then combined with citric acid, aspartame, orange flavor, mirtazapine, and mannitol and mixed again in the GEMCO blender (General Machine Company of New Jersey Inc., Middlesex, N.J.) with the agitator off. After 15 minutes, crospovidone is added and the mixture is blended for another 15 minutes. The mixture is then screened through #20 mesh and mixed again for 18 minutes. Sodium stearyl fumarate is then added and the mixture is mixed for seven more minutes. At which time, magnesium stearate, which has been passed through a #30 mesh screen, is added, and the mixing continues for a final seven minutes. The mixture is then compressed into tablets on a tablet press, e.g., KIKUSUI (Kikusui Tablet Press, Toms River, N.J.) using 13/32 inch flat-face bevel edge (FFBE) tooling for forming 15 mg mirtazapine orally disintegrating tablets, and 16/32 inch FFBE tooling for forming 30 mg mirtazapine orally disintegrating tablets.

Example 2

The procedure of Example 1 was used to make the following 15 mg mirtazapine orally disintegrating pharmaceutical tablet:

TABLE 2

15 mg mirtazapine orally disintegrating tablet

| Ingredient | Milligrams/Tablet | % |
|---|---|---|
| Mirtazapine | 15 mg | 6.0 |
| Tartaric Acid | 15 mg | 6.0 |
| Microcrystalline Cellulose | 15 mg | 6.0 |
| Citric Acid | 21 mg | 8.4 |
| Aspartame | 10 mg | 4.0 |
| Orange Flavor | 1.5 mg | 0.6 |
| Mannitol | 109 mg | 43.6 |
| Crospovidone | 60 mg | 24.0 |
| Magnesium Stearate | 1.5 mg | 0.6 |
| Sodium Stearyl Fumarate | 2 mg | 0.8 |
| Net Tablet weight | 250 mg | 100 |

Example 3

The procedure of Example 1 was also used to make the following 30 mg mirtazapine orally disintegrating pharmaceutical tablet:

TABLE 3

30 mg mirtazapine orally disintegrating tablet

| Ingredient | Milligrams/Tablet |
|---|---|
| Mirtazapine | 30 mg |
| Tartaric Acid | 30 mg |
| Microcrystalline Cellulose | 30 mg |
| Citric Acid | 42 mg |
| Aspartame | 20 mg |
| Orange Flavor | 3 mg |
| Mannitol | 218 mg |
| Crospovidone | 120 mg |
| Magnesium Stearate | 3 mg |
| Sodium Stearyl Fumarate | 4 mg |
| Net Tablet weight | 500 mg |

Example 4

Table 4 depicts the comparative hardness (kp) for mirtazapine tablets for the 15 and 30 mg dosage forms tablets of Examples 2 and 3. The 15 mg and 30 mg tablets were determined to have a hardness from about 2.6 to about 1.8 and from 2.7 kp to about 1.7 kp, respectively, at 25° C. and 60% relative humidity (RH) when the tablets were exposed to the environment for up to 24 hours. Table 4 shows that at control room temperature, the hardness of the reference tablets decreased rapidly over a period of time (i.e. the tablet breaks down and gets mushy).

TABLE 4

Comparative Hardness (Kp) data for Mirtazapine Tablets, 15 and 30 mg Barr vs. Reference at 25° C./60% RH

| Time (Hours) | 15 mg (Example 2), kp | Reference 1, kp | 30 mg (Example 3), kp | Reference 2, kp |
|---|---|---|---|---|
| 0 | 2.6 | 1.8 | 2.7 | 1.6 |
| 2 | 1.2 | 0.6 | 1.2 | 0.5 |
| 6 | 1.2 | 0.3 | 1.2 | 0.3 |
| 24 | 1.2 | 0.3 | 1.2 | Powder |
| 48 | 1.8 | 0.5 | 1.7 | Powder |

Table 5 shows that the hardness of the 15 mg and 30 mg dosage forms at 40° C. and 75% RH ranged from about 2.8 kp to about 0.8 kp and from about 2.7 kp to about 1.1 kp, respectively, when the tablets were exposed to the environment for up to one hour. Table 5 demonstrates that the physical integrity of the 30 mg mirtazapine tablet of the present invention is maintained under harsher conditions and is thus not spoiled. This physical property of the tablet is advantageous to users of the tablet in hot and humid climates.

TABLE 5

Comparative Hardness (Kp) data for 15 mg and 30 mg Mirtazapine Tablets vs. Reference at 40° C./75% RH

| Time (Hours) | Barr (15 mg), kp | Reference (15 mg), kp | Barr (30 mg), kp | Reference (30 mg), kp |
|---|---|---|---|---|
| 0 | 2.8 | 1.9 | 2.7 | 1.9 |
| 0.25 | 1.5 | 0.6 | 2.0 | 0.5 |
| 0.5 | 1.5 | 0.4 | 1.4 | 0.4 |
| 0.75 | 0.9 | 0.4 | 1.1 | 0.4 |
| 1.0 | 0.8 | 0.4 | 1.1 | 0.4 |

Table 6 depicts the dissolution profile for the 15 mg dosage form, which was obtained in a dissolution medium of 900 mL of 0.01 N HCl with a paddle speed of 50 rpm. The table shows that about 100% of the 15 mg dosage form dissolves in five minutes.

TABLE 6

Comparative Dissolution Profile for 15 mg Mirtazapine Orally Disintegrating Tablets Dissolution Medium: 0.01 N HCl 900 mL, 50 rpm, Paddle (Percent Dissolved)

| Time (mins) | Reference 1 0010300046 | 15 mg Tablet (Example 2) 202411001R |
|---|---|---|
| 0 | 0 | 0 |
| 5 | 97 | 101 |
| 10 | 103 | 101 |
| 20 | 103 | 101 |
| 30 | 103 | 101 |
| 45 | 103 | 101 |
| 60 | 103 | 101 |

Table 7 depicts the dissolution profile for a 30 mg dosage form of the present invention which was obtained in a dissolution medium of 900 mL of 0.01 N HCl with a paddle speed of 50 rpm. The table shows that about 99% of the 30 mg dosage form dissolves in five minutes.

TABLE 7

Comparative Dissolution Profile for Mirtazapine Orally Disintegrating Tablets 30 mg Dissolution Medium: 0.01 N HCl 900 mL, 50 rpm, Paddle Dissolution Medium: 0.01 N HCl 900 mL, 50 rpm, Paddle (Percent Dissolved)

| Time (mins) | Reference 1 0010300046 | 30 mg Tablet (Example 3) 202411001R |
|---|---|---|
| 0 | 0 | 0 |
| 5 | 90 | 99 |
| 10 | 101 | 99 |
| 20 | 102 | 99 |
| 30 | 102 | 99 |
| 45 | 102 | 99 |

Example 5

Table 8 shows 15 mg, 30 mg and 45 mg mirtazapine orally disintegrating tablet formulations prepared by the process shown in FIG. 2.

TABLE 8

Mirtazapine orally disintegrating tablets

| # | INGREDIENT | 15 mg Tablet (mg) | 30 mg Tablet (mg) | 45 mg Tablet (mg) | % |
|---|---|---|---|---|---|
| 1 | Mirtazapine | 15.00 | 30.00 | 45.00 | 9.375 |
| 2 | Microcrystalline cellulose, NF (AVICEL PH101) | 10.00 | 20.00 | 30.00 | 6.25 |
| 3 | N-C NATURAL & ARTIFICIAL ORANGE FLAVOR (POWDER) | 1.000 | 2.000 | 3.000 | 0.625 |
| 4 | Crospovidone, NF (POLYPLASDONE XL) | 42.00 | 84.00 | 126.0 | 26.25 |

TABLE 8-continued

Mirtazapine orally disintegrating tablets

| # | INGREDIENT | 15 mg Tablet (mg) | 30 mg Tablet (mg) | 45 mg Tablet (mg) | % |
|---|---|---|---|---|---|
| 5 | Mannitol, USP (PARTECK M200) | 76.30 | 152.6 | 228.9 | 47.68 |
| 6 | Colloidal Silicon Dioxide, NF (CAB-O-SIL) | 1.700 | 3.400 | 5.100 | 1.06 |
| 7 | Magnesium stearate, NF | 1.500 | 3.000 | 4.500 | 0.937 |
| 8 | Sodium stearyl fumarate, NF | 1.500 | 3.000 | 4.500 | 0.937 |
| 9 | Xylitol (XYLISORB 300) | 5.000 | 10.00 | 15.00 | 3.125 |
| 10 | Aspartame, USP (NUTRA SWEET powder) | 6.000 | 12.00 | 18.00 | 3.75 |
|  | Total | 160.0 | 320 | 480 |  |

Table 9 provides the disintegration time, friability and tablet hardness (kp) for the 15 mg, 30 mg and 45 mg formulations shown in Table 8. Friability, which is a measure of the crumbliness of the tablet is also provided. As seen in Table 8, friability of the tablets at a hardness lesser than about 1.5 kp is more than 2%.

TABLE 9

Disintegration time and friability

| Tablet Hardness (kp) | Disintegration time (sec) | | | Friability (%) | | |
|---|---|---|---|---|---|---|
|  | 15 mg | 30 mg | 45 mg | 15 mg | 30 mg | 45 mg |
| 0.5 | 3.3 | 5.2 | 6.33 | 100 | 100 | 100 |
| 1 | 4 | 5 | 6.4 | 100 | 100 | 100 |
| 1.5 | 4.7 | 6.7 | 6.7 | 0.1 | 60.6 | 100 |
| 2 | 5.7 | 6.3 | 5.7 | <0.1 | 0.7 | 48 |
| 2.5 | 7.7 | 7.3 | 7 | <0.1 | 0.7 | 18 |
| 3 | — | 7.33 | 8 | <0.1 | 0.1 | 2 |

Figure 3:
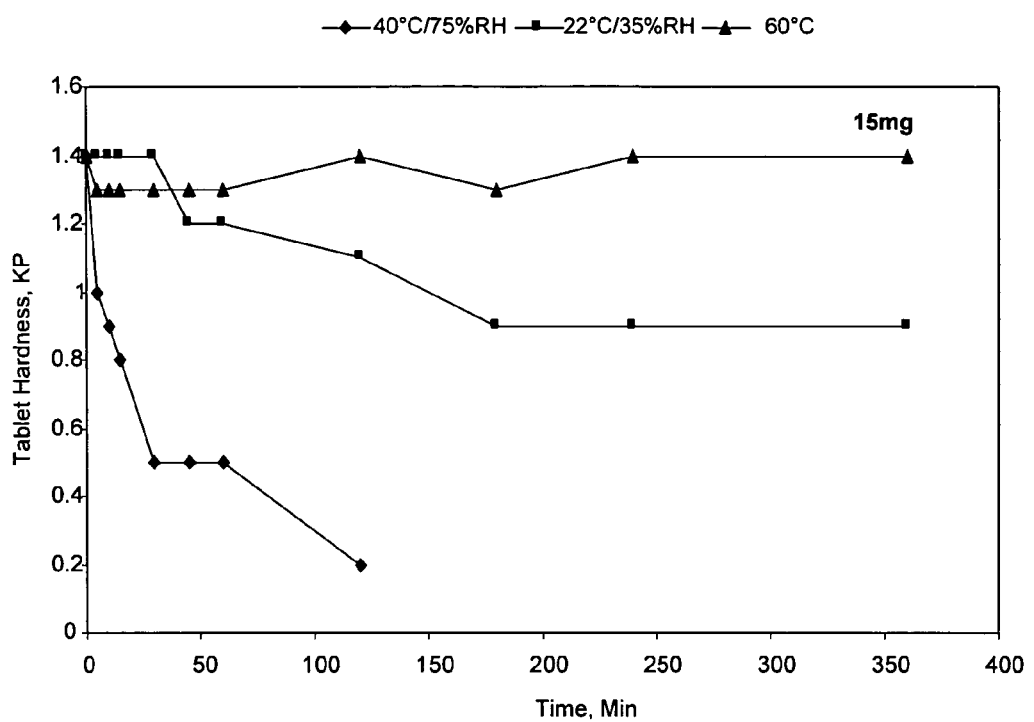
FIG. 3 is a graph showing the effect of temperature and humidity on the 15 mg mirtazapine orally disintegrating tablets provided in Table 8.
Figure 4:
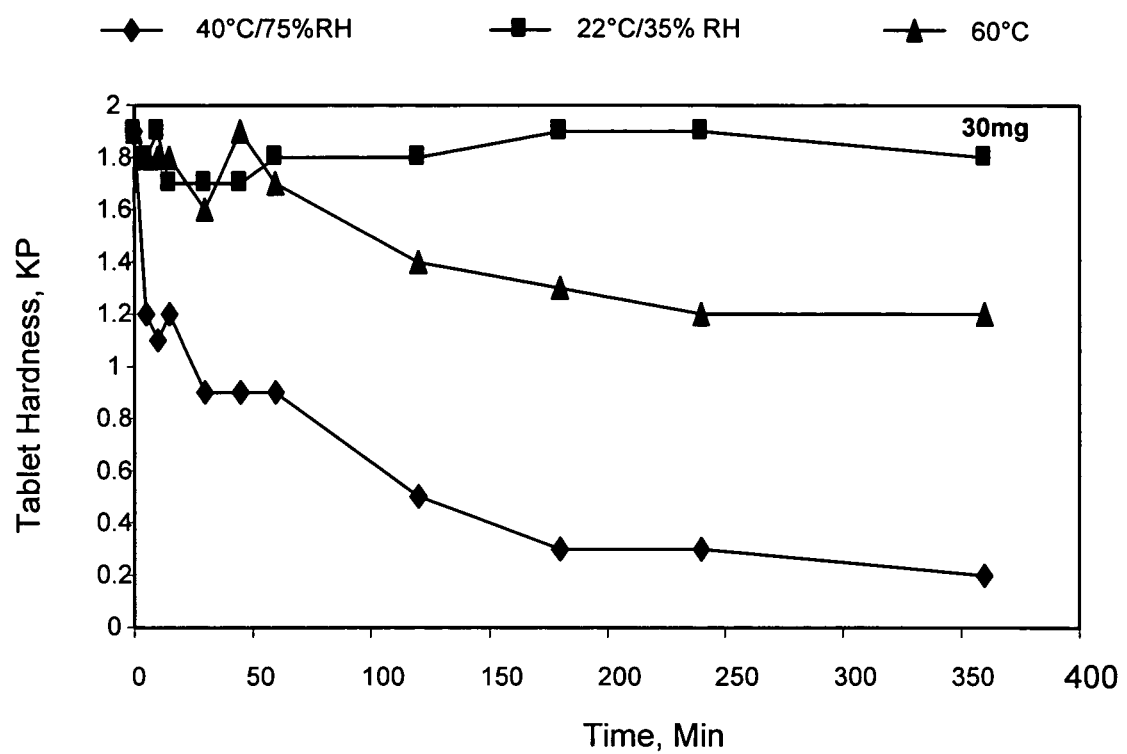
FIG. 4 is a graph showing the effect of temperature and humidity on the 30 mg mirtazapine orally disintegrating tablets provided in Table 8.
Figure 5:
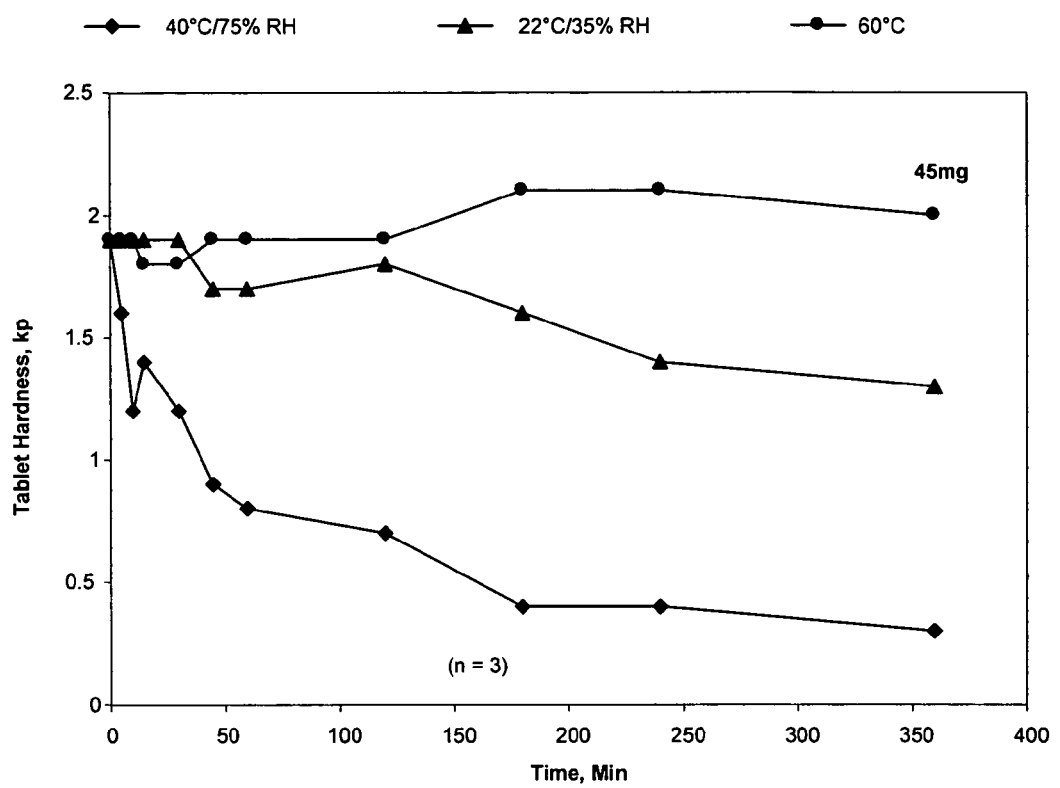
FIG. 5 is a graph showing the effect of temperature and humidity on the 45 mg mirtazapine orally disintegrating tablets provided in Table 8.

Tables 10, 11 and 12 provide the effect of temperature and moisture (also referred to as relative humidity or RH) on the hardness of the 15 mg, 30 mg and 45 mg formulations provided in Table 8. The results in Tables 10, 11 and 12 are graphically depicted in FIGS. 3, 4 and 5. As seen in Table 10, the hardness of 15 mg tablets exposed to 22° C./35% RH for 6 hr was about 64% of the hardness of the tablets exposed for 0 min, i.e., the hardness of the tablet after exposure to 22° C./35% RH for 6 hr was more than 50% of the hardness of the tablet exposed for 0 min. Further, the hardness of the 15 mg tablet exposed to 40° C./75% RH for 15 min was about 57% of the hardness after exposure for 0 min, i.e., the hardness of the tablet after exposure to 40° C./75% RH for 15 min was more than 50% of the hardness of the unexposed 15 mg tablet.

Table 11 shows that the hardness of the 30 mg after exposure to 22° C./35% RH for 6 hr, or to 40° C./75% RH for 15 min was more than 50% of the hardness of the 30 mg tablet exposed for 0 min to either condition.

Table 12 shows that the hardness of the 45 mg after exposure to 22° C./35% RH for 6 hr, or to 40° C./75% RH for 15 min was more than 50% of the hardness of the 45 mg tablet exposed for 0 min to either condition.

TABLE 10

Effect of temperature/moisture on hardness of the 15 mg formulation

| | Hardness (kp) | | |
|---|---|---|---|
| Time (min) | 15 mg Tablet 40° C./75% RH | 15 mg Tablet 22° C./35% RH | 15 mg Tablet 60° C. |
| 0 | 1.4 | 1.4 | 1.4 |
| 5 | 1.0 | 1.4 | 1.3 |
| 10 | 0.9 | 1.4 | 1.3 |
| 15 | 0.8 | 1.4 | 1.3 |
| 30 | 0.5 | 1.4 | 1.3 |
| 45 | 0.5 | 1.2 | 1.3 |
| 60 | 0.5 | 1.2 | 1.3 |
| 120 | 0.2 | 1.1 | 1.4 |
| 180 | <0.1 | 0.9 | 1.3 |
| 240 | <0.1 | 0.9 | 1.4 |
| 360 | <0.1 | 0.9 | 1.4 |

TABLE 11

Effect of temperature/moisture on hardness of the 30 mg formulation

| | Hardness (kp) | | |
|---|---|---|---|
| Time (min) | 30 mg Tablet 40° C./75% RH | 30 mg Tablet 22° C./35% RH | 30 mg Tablet 60° C. |
| 0 | 1.9 | 1.9 | 1.9 |
| 5 | 1.2 | 1.8 | 1.8 |
| 10 | 1.1 | 1.9 | 1.8 |
| 15 | 1.2 | 1.7 | 1.8 |
| 30 | 0.9 | 1.7 | 1.6 |
| 45 | 0.9 | 1.7 | 1.9 |
| 60 | 0.9 | 1.8 | 1.7 |
| 120 | 0.5 | 1.8 | 1.4 |
| 180 | 0.3 | 1.9 | 1.3 |
| 240 | 0.3 | 1.9 | 1.2 |
| 360 | 0.2 | 1.8 | 1.2 |

TABLE 12

Effect of temperature/moisture on hardness of the 45 mg formulation

| | Hardness (kp) | | |
|---|---|---|---|
| Time (min) | 45 mg Tablet 40° C./75% RH | 45 mg Tablet 22° C./35% RH | 45 mg Tablet 60° C. |
| 0 | 1.9 | 1.9 | 1.9 |
| 5 | 1.6 | 1.9 | 1.9 |
| 10 | 1.2 | 1.9 | 1.9 |
| 15 | 1.4 | 1.8 | 1.9 |
| 30 | 1.2 | 1.8 | 1.9 |
| 45 | 0.9 | 1.9 | 1.7 |
| 60 | 0.8 | 1.9 | 1.7 |
| 120 | 0.7 | 1.9 | 1.8 |
| 180 | 0.4 | 2.1 | 1.6 |
| 240 | 0.4 | 2.1 | 1.4 |
| 360 | 0.3 | 2.0 | 1.3 |

Example 8

Table 13 shows 15 mg, 30 mg and 45 mg mirtazapine orally disintegrating tablets containing calcium silicate, which were prepared by the process shown in FIG. 2.

TABLE 13

Mirtazapine orally disintegrating tablets containing calcium silicate

| INGREDIENT | 15 mg Tablet | 30 mg Tablet | 45 mg Tablet | % |
|---|---|---|---|---|
| 1 Mirtazapine | 15.00 | 30.00 | 45.00 | 9.375 |
| 2 Microcrystalline cellulose, NF (AVICEL PH101) | 10.00 | 20.00 | 30.00 | 6.25 |
| 3 N-C NATURAL & ARTIFICIAL ORANGE FLAVOR (POWDER) | 1.000 | 2.000 | 3.000 | 0.625 |
| 4 Crospovidone, NF (POLYPLASDONE XL) | 21.00 | 42.00 | 63.00 | 13.125 |
| 5 Calcium Silicate (FM 1000) | 21.00 | 42.00 | 63.00 | 13.125 |
| 6 Mannitol, USP (PARTECK M200) | 76.30 | 152.6 | 228.9 | 47.6 |
| 7 Colloidal Silicon Dioxide, NF (CAB-O-SIL) | 1.700 | 3.400 | 5.100 | 1.06 |
| 8 Magnesium stearate, NF | 1.500 | 3.000 | 4.500 | 0.937 |
| 9 Sodium stearyl fumarate, NF | 1.500 | 3.000 | 4.500 | 0.937 |
| 10 Xylitol (XYLISORB 300) | 5.000 | 10.00 | 15.00 | 3.125 |
| 11 Aspartame, USP (NUTRA SWEET powder) | 6.000 | 12.00 | 18.00 | 3.75 |
| Total | 160.0 | 320.0 | 480.0 | 100 |

Table 14 provides the relationship between hardness of the 15 mg tablet of Table 10 and the disintegration time (DT).

TABLE 14

Tablet disintegration time vs. hardness

| Tablet Hardness (kp) | DT (sec) | Friability (%) |
|---|---|---|
| 0.5 | 3.6 | 100 |
| 1 | 3.3 | 100 |
| 1.5 | 4 | 5.3 |
| 2 | 3 | 0.1 |
| 2.5 | 4.8 | <0.1 |
| 3 | 5.7 | <0.1 |
| 4 | 6.3 | <0.1 |
| 5 | 8.3 | <0.1 |

One skilled in the art would understand that, despite the full description provided herein, the present invention can be performed within a wide and equivalent range of conditions, formulations, and other parameters without affecting the scope of the invention or any embodiment thereof. All patents and publications cited herein are fully incorporated by reference herein in their entirety.

What is claimed is:

1. A method for preparing a non-effervescent, orally disintegrating mirtazapine tablet consisting of:
   a) preparing a dry mixture consisting of:
      i) about 0.5% to about 10% of mirtazipine;
      ii) about 35% to about 65% by weight of mannitol;
      iii) about 15% to about 35% by weight of crosspovidone;
      iv) about 5 to about 15% of microcrystalline cellulose;
      v) about 0.5% to about 4% at least one lubricant;
      vi) 0 to about 10% of a salivating agent;
      vii) colloidal silicon dioxide;
      viii) optionally a coloring agent;
      xi) optionally a flavoring agent; and
      x) optionally a sweetner;
   b) compressing the dry mixture into 15 mg, 30 mg or 45 mg mirtazipine tablets with a hardness of about 1.5 kp to about 3 kp and a tablet hardness greater than 1.0 kp after exposure for 24 hours at 25° C. and 60% relative humidity and greater than about 0.8 kp after exposure for 60 minutes at 40° C. and 75% relative humidity.

2. A tablet prepared according to the method of claim 1 that disintegrates in about 3 to about 8 seconds.

3. A tablet prepared according to the method of claim 1.

4. A tablet prepared according to the method of claim 1 wherein the hardness is about 2 kp to about 3 kp.

* * * * *